US006498195B2

(12) United States Patent
Rosen et al.

(10) Patent No.: US 6,498,195 B2
(45) Date of Patent: Dec. 24, 2002

(54) USE OF 1-PROPANONE-1-(2,4-DIHYDROXYPHENYL)-3-HYDROXY-3-(4'-HYDROXYPHENYL) AS AN ANTICARCINOGENIC AGENT

(75) Inventors: Robert T. Rosen, Monroe Township, NJ (US); Chi-Tang Ho, East Brunswick, NJ (US); Robert S. DiPaola, Long Valley, NJ (US); Mohamed M. Rafi, Highland Park, NJ (US); Bret C. Vastano, Lonaka Harbor, NJ (US); Geetha Ghai, Murray Hill, NJ (US)

(73) Assignees: Rutgers, The State University of New Jersey, New Brunswick, NJ (US); University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/880,296

(22) Filed: Jun. 13, 2001

(65) Prior Publication Data

US 2002/0022665 A1 Feb. 21, 2002

Related U.S. Application Data

(60) Provisional application No. 60/211,266, filed on Jun. 13, 2000.

(51) Int. Cl.[7] ............................................. A61K 31/72
(52) U.S. Cl. .................. 514/688; 514/689; 568/325; 568/331; 568/337
(58) Field of Search ................ 568/325, 331, 568/334, 337; 514/688, 689

(56) References Cited

FOREIGN PATENT DOCUMENTS

EP 0998939 A1 * 5/2000
JP 02204495 8/1990

OTHER PUBLICATIONS

Yoshida et al, Two Polyphenol Glycosides and Tannins from Rosa cymosa, Jun. 1992, Phytochemistry, vol. 32, No. 4, pp. 1033–1036.*

Press Release, AACR–NCI–EORTC International Conference, New Compound Extracted From Licorice Root Shows Antitumor Activity in Acute Leukemia, Breast and Prostate Cancer (Nov. 17, 1999), available at http://www.aacr.org/1000/1100/1200ae.html (last visited on Apr. 3, 2002).

Armanini, D., et al., "Reduction of Serum Testosterone in Men by Licorice", *N. Eng. J. Med.*, 1999, vol. 341, p. 1158.

Combest, W. L., "Herbal pharmacy: Licorice", *U.S. Pharmacist*, 1998, vol. 23:4, available at http://www.uspharmacist.com/NewLook/DisplayArticle.cfm?item_num=106 (last visited on May 6, 2002).

DiPaola, R.S., et al., "Phase I clinical and pharmacological study of 13–cis–retinoic acid, interferon alfa, and paclitaxel in patients with prostate cancer and other advanced malignancies", *J. Clin. Oncol.*, 1999, vol. 17, pp. 2213–2218.

DiPaola, R.S., et al., "Clinical and Biologic Activity of an Estrogenic Herbal Combination (PC–SPES) in Prostate Cancer", *N. Engl. J. Med.*, 1998, vol. 339, No. 12, pp. 785–791.

Edwards, M.L., et al., "Chalcones: A New Class of Antimitotic Agents", *J. Med. Chem.*, 1990, vol. 33, pp. 1948–1954.

(List continued on next page.)

Primary Examiner—Paul J. Killos
Assistant Examiner—Taylor V Oh
(74) Attorney, Agent, or Firm—ReedSmith LLP

(57) ABSTRACT

Compositions and methods are provided for prevention and treatment of cancer. The compositions comprise pure hydroxylated chalcone compounds of licorice root (*Glycyrrhiza glabra*) including 1-propanone-1-(2,4-dihydroxyphenyl)-3-hydroxy-3-(4'-hydroxyphenyl).

4 Claims, 1 Drawing Sheet

A

B

C

OTHER PUBLICATIONS

Goldberg, D.M., et al., "Resveratrol Glucosides are Important Components of Commercial Wines", *Am. Jour. of Enol. Vitic.,* vol. 47, No. 4, 1996, pp. 415–420.

Haldar, S., et al., "Inactivation of Bcl–2 by Phosphorylation", *Proc. Natl. Acad. Sci. USA,* 1995, vol. 92, pp. 4507–4511.

Haldar, S., et al., "Taxol Induces bcl–2 Phosphorylation and Death of Prostate Cancer Cells", *Cancer Res.,* 1996, vol. 56, pp. 1253–1255.

Hsieh, T., et al., "Regulation of androgen receptor (AR) and prostate specific antigen (PSA) expression in the androgen–responsive human prostate LNCaP cells by ethanolic extracts of the Chinese herbal preparation, PC–SPES", *Biochem. Mol. Biol. Int.,* 1977, vol. 42, pp. 534–544.

Iwata, S., et al., "Antitumorigenic Activities of Chalcones. I. Inhibitory Effects of Chalcone Derivatives on $^{32}$Pi–Incorporation into Phospholipids of HeLa Cells Promoted by 12–O–Tetradecanoyl–phorbol 13–Acetate (TPA)", *Biol. Pharm. Bull,* vol. 18, No. 12, 18(12) pp. 1710–1713 (1995).

Kobayashi, S., et al., "Inhibitory Effect of Isoliquiritin, a Compound in Licorice Root, on Angiogenesis in Vivo and Tube Formation in Vitro", *Biol. Phar. Bull.,* 1995, vol. 18, pp. 1382–1386.

Mitscher, L.A., et al., "Antimicrobial Agents From Higher Plants. Antimicrobial Isoflavanoids and related substances from *Glycyrrhiza Glabra* L. Var. *Typica"*, *J. Nat. Prod..* 1980, vol. 43, pp. 259–269.

Palagina, M.V., et al., "Pulmonary Metabolism and Its Correction in Radiotherapy of Thoracic Tumors", *Ter. Arkh.,* 1999, vol. 71, pp. 45–48. Foreign language—English Abstract.

Rafi, M.M., et al., "Modulation of bcl–2 and Cytotoxicity of Licochalcone–A, a Novel Estrogenic Flavonoid", *Proceedings of the 1999 AACR–NCI–EORTC International Conference,* Abstract #263; published as a supplement to *Clinical Cancer Research,* 1999, vol. 5, ISSN. 1078–0432.

Rafi, M.M., et al., "Modulation of bcl–2 and Cytotoxicity by Licochalcone–A, a Novel Estrogenic Flavonoid", *Anticancer Res.,* 2000, vol. 20, No. 4, pp. 2653–2658.

Rafi, M.M., et al., "Novel Derivative from the Licorice Induces Apoptosis and Phosphorylates Bcl–2", 2001, Proceedings from the American Association of Cancer Research, vol. 42, Annual Meeting in New Orleans, LA, Mar. 24–28 (2001), Abstract #1009.

Rafi, M.M., et al., "Modulation of bcl–2 by flavonoids isolated from *glycyrrhiza inflata"*, 2000, Proceedings of the American Association for Cancer Research, Annual Meeting, Mar., (2000), Abstract #4692.

Rafi, M.M., et al., "Licochalcone–A: A novel phytoestrogen with antitumor activity in Breast and prostate tumor cell lines", 1999, Proceedings from the American Society of Clinical Oncology, Annual Meeting in Atlanta, GA, May 15–18 (1999), vol. 18 Abstract #712.

Raggi, M.A., et al., "Studio dell' effetto coleretico della liquirizia: identificazione e determinazione di componenti della *Glycyrrhiza glabra* farmacologicamente attivi", *Boll Chim. Far.,* 1995, vol. 134, pp. 634–638. Foreign Language—English Abstract.

Reed, J.C., "Double Identity for Proteins of the Bcl–2 Family", *Nature,* 1997, vol. 387, pp. 773–776.

Scudiero, D.A., et al., "Evaluation of a Soluble Tetrazolium/Formazan Assay for Cell Growth and Drug Sensitivity in Culture Using Human and Other Tumor Cell Lines", *Cancer Res.,* 1988, vol. 48, pp. 4827–4833.

Shibata, S., "Antitumorigenic Chalcones", *Stem Cells,* 1994, vol. 12, pp. 44–52.

Small, E., et al., "PC–SPES in Prostate Cancer", *N. Eng. J. Med.,* 1999, vol. 340, No. 7, pp. 785–791.

de la Taille, A., et al., "Effects of a phytotherapeutic agent, PC–SPES, on prostate cancer: a preliminary investigation on human cell lines and patients", *BJU Int.,* 1999, vol. 84, pp. 845–850.

Tiwari, R.K., et al., "Anti–tumor effects of PC–SPES, an herbal formulation in prostate cancer", *Int. J. Oncol.,* 1999, vol. 14, pp. 713–719.

Vastano, B.C., et al., "Isolation and Identification of Bioactive Compounds from Licorice (*Glycyrrhiza glabra*)", $221^{st}$, ACS National Meeting, San Diego, CA, Apr. 1–5, 2001, *Am. Chem. Soc.,* 2001, vol. 221, p. 121.

Vaya, J., et al., "Antioxidant constituents from licorice roots: isolation, structure elucidation and antioxidative capacity toward LDL oxidation", *Free Radical Biol. Med.,* 1997, vol. 2, pp. 302–313.

Yamamoto, S., et al., "The Potent Anti–Tumor–Promoting Agent Isoliquiritigenin", *Carcinogenesis,* 1991, vol. 12, No. 2 pp. 317–323.

Yokota, T., et al., "The Inhibitory Effect of Glabrindin from Licorice Extracts on Melanogenesis and Inflammation", *Pigment Cell Res.,* 1998, vol. 11, pp. 355–361.

Zhai, L., et al., "The Antileishmanial Agent Lichochalcone A Interferes with the Function of Parasite Mitochondria", *Antimicrob. Agents Chemotherop.,* 1995, vol. 39, pp. 2742–2748.

Zhang, C.C., "The Role of MAP4 expression in the Sensitivity to Paclitaxel and Resistance to Vinca Alkaloids in p53 Mutant Cells", *Oncogene,* 1998, vol. 16, pp. 1617–1624.

* cited by examiner

A

B

C

USE OF 1-PROPANONE-1-(2,4-DIHYDROXYPHENYL)-3-HYDROXY-3-(4'-HYDROXYPHENYL) AS AN ANTICARCINOGENIC AGENT

INTRODUCTION

This application claims the benefit of priority from Provisional Application Serial No. 60/211,266 filed Jun. 13, 2000.

BACKGROUND OF THE INVENTION

Herbal products have gained popularity for their use in the treatment of diseases in humans. Although the clinical effect of most herbal products is unknown, many herbs contain derivatives with biological activity. One such herb is licorice root. Extracts of licorice root have been shown to have biological activity that includes antioxidant activity (Palagina, M. V. et al. 1999. *Ter. Arkh.* 71:45–48), inhibition of melanin synthesis (Yokota, T. et al. 1998. *Pigment Cell Res.* 11:355–361), inhibition of angiogenesis (Kobayashi, S. et al. 1995. *Biol. Phar,. Bull.* 18:1382–1386), anti-microbial activity (Mitscher, L. A. et al. 1980. *J. Nat. Prod.* 43: 259–269), anti-parasitic activity (Zhai, L. et al. 1995. *Antimicrob. Agents Chemotherap.* 39:2742–2748), and anti-tumor activity (Shibata, S. 1994. *Stem Cells* 12:44–52). Several compounds responsible for the various biological effects have been isolated. Examples of such compounds include glabridin (Yokota, T. et al. 1998. *Pigment Cell Res.* 11:355–361), isoliquiritin (Kobayashi, S. et al. 1995. *Biol. Pharm. Bull.* 18:1382–1386), glycyrrhizin (Raggi, M. A. et al. 1995. *Boll. Chim. Farm.* 134:634–638), and licochalcone A, a non-hydroxylated chalcone compound (Shibata, S. 1994. *Stem Cells* 12:44–52).

Recent studies with a combination of eight herbs, that included licorice root, called PC-SPES, has been shown to have potent clinical and biological activity (DiPaola, R. S. et al. 1998. *N. Engl. J. Med.* 339:785–791). PC-SPES showed anti-prostate cancer activity which was attributable to phytoestrogens that produced a chemical castration. Another study demonstrated that licorice root alone was capable of decreasing circulating testosterone levels in men (Armanini, D. et al. 1999. *N. Engl. J. Med.* 341:1158). Additional studies in patients have demonstrated PC-SPES to have anti-tumor activity refractory to chemical castration, thus indicating that other mechanisms may be responsible for the anti-tumorigenic activity of this licorice root-herbal combination therapy (Small, E. et al. 1999. *N. Engl. J. Med.* 340(7):785–791).

PC-SPES extracts have also been shown to induce apoptosis in tumor cell lines and decreased the expression of bcl-2. Bcl-2 is a 26 kDa protein that blocks cell death by inhibiting cytochrome c release from mitochondria, a critical event in the apoptotic pathway. Overexpression of bcl-2 protects cells from death promoting stimuli, whereas lowering bcl-2 levels increases cell death and sensitivity to chemotherapy (Reed, J. C. 1997. *Nature* 387:773–776). Recent studies suggest that drugs which decrease bcl-2 expression, or inactivate the molecule through phosphorylation, induce apoptosis. For example, paclitaxel, docetaxol, vincristine, and vinblastine alter microtubule structure and induce apoptosis in association with bcl-2 phosphorylation (Hadlar, S. et al. 1996. *Cancer Res.* 56:1253; Haldar, S. et al. 1995. *Proc. Natl. Acad. Sci. USA* 92:4507–4511).

It has now been found that compounds extracted from licorice root, in particular hydroxylated chalcones, have activity consistent with induction of apoptosis and potential activity as anti-tumorigenic and anti-carcinogenic agents.

SUMMARY OF THE INVENTION

An object of the present invention is to provide a hydroxylated chalcone compound extracted and purified from *Glycyrrhiza glabra*. In a preferred embodiment the compound comprises 1-propanone-1-(2,4-dihydroxyphenyl)-3-hydroxy-3-(4-hydroxyphenyl).

Another object of the present invention is to provide a method of inducing phosphorylation of bcl-2 comprising contacting cells or tissues with a hydroxylated chalcone compound.

Yet another object of the present invention is to provide a method of inducing apoptosis in cells or tissues comprising contacting cells or tissues with a hydroxylated chalcone compound.

Also included in the present invention are methods for inhibiting tumor cell growth and preventing and treating cancer via contacting tumor cells or tissues with an effective amount of a hydroxylated chalcone compound.

DESCRIPTION OF THE DRAWINGS

FIG. 1A is the structure of the parent compound, 1-propanone-1-(2,4-dihydroxyphenyl)-3-hydroxy-3-(4'-hydroxyphenyl). FIG. 1B depicts a glycosylated derivative of the parent compound which is referred to herein as 1-propanone-1-(2,4-dihydroxyphenyl)-3-hydroxy-3-(4'-hydroxyphenyl-4'o-beta-D-glucapyranoside). FIG. 1C is a second glycosylated derivative of the parent compound which is referred to herein as 1-propanone-1-(2,4-dihydroxyphenyl-4'-o-beta-D-glucopyranoside)-3-hydroxy-3-(4'-hydroxyphenyl).

DETAILED DESCRIPTION OF THE INVENTION

A specific component of licorice root extract, a hydroxylated chalcone, has now been identified which has biological activity consistent with anti-tumorigenic effects in animals, including humans. It is believed that this licorice root extract component can be used as an anti-cancer agent in the prevention and treatment of cancer in animals, including humans.

The hydroxylated chalcones of the present invention were identified by extracting licorice root with methanol, ethanol, DMSO or ethyl acetate. Crude extract fractions were collected and the effects of various fractions of whole licorice root were assessed by immunoblotting. Licorice root extracted with ethyl acetate, DMSO, or ethanol induced bcl-2 phosphorylation as demonstrated by a slower migrating band as compared to the vehicle control (ethanol alone) or a water extract.

Previous studies have confirmed an association between bcl-2 phosphorylation and cell-cycle arrest at G2/M. Accordingly, the effects of the various licorice root extracts on cell cycle were also assessed. Licorice root extract induced G2/M cell cycle arrest in a similar manner to paclitaxel (control). Thus, these results demonstrate that the licorice root extract has biological activity similar to known anti-microtubule drugs.

Figure 1:
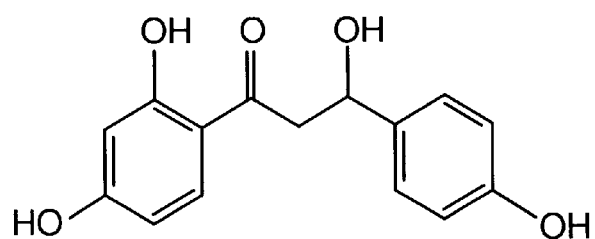
FIG. 1 depicts structures of several hydroxylated chalcones of the present invention that were identified by mass spectrometry and NMR.
Figure 1:
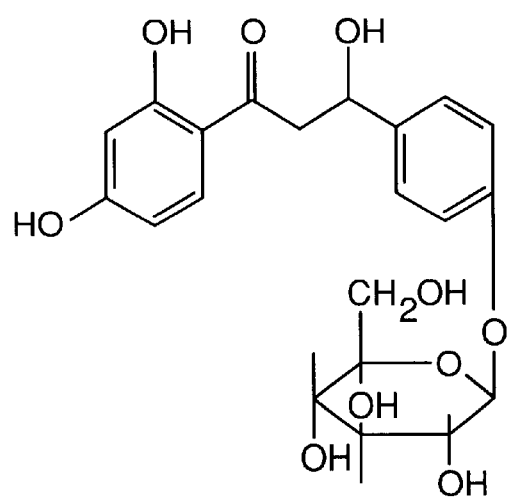
Figure 1:
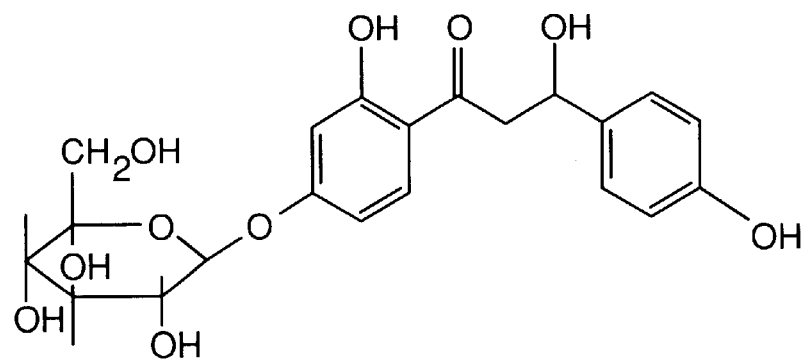

To identify the active component in the licorice root extract capable of bcl-2 phosphorylation, fractions were collected and assessed by HPLC. The extract contained multiple derivatives. Accordingly, the focus was placed on the three major peaks determined by HPLC. Fractions eluted from major peaks 1, 2, and 3 were shown to induce bcl-2 phosphorylation in a manner similar to paclitaxel-treated controls. Analysis by NMR and mass spectrometry revealed that peak 3 contained a hydroxylated chalcone compound (referred to herein as DC and depicted in FIG. 1A). Peaks 1 and 2 were two glycosylated derivatives of DC (FIGS. 1B and 1C, respectively). Other polyphenol structures found in various foods, such as resveratrol, an estrogenic compound isolated from red wine (Goldberg, D. M. et al. 1996. *Am. Jour. of Enol. Vitic.* 47:415–420), have been suggested as potential anti-cancer and chemopreventative agents. A DC-type compound has also been isolated from another natural product, Rosa cymosa (Yoshida et al. 1993. *Phytochemistry* 32:1033–1036), However, the biological activity of this DC-type compound has not been determined.

The activity of purified DC was determined in additional testing. DC was shown to induce phosphorylation of bcl-2 in both MCF-7 and DUPro-1 tumor cells. In addition, the pure DC induced G2/M cell cycle arrest similar to whole licorice root extracts. In these experiments MCF-7 tumor cells were treated with DC and assessed by flow cytometry. DC induced a G2/M cell cycle arrest in a manner similar to the known anti-microtubule agent paclitaxel. However, DC was shown to induce microtubule fragmentation in a manner similar to vinblastine, while paclitaxel has been shown to induce microtubule bundles. Therefore, DC is actually a microtubule destabilizer, more similar to vinblastine. These data demonstrate that a hydroxylated chalcone compound with no methoxy groups still has significant anti-microtubule activity similar to chalcone structures with multiple methoxy groups (Edwards, M. L. et al. 1990. *J. Med. Chem.* 33:1948–1954).

The cytotoxicity of DC was then assessed in an apoptosis assay. In this assay, tumor cells were treated with pure DC and cell viability and apoptosis responses were assessed. DC induced apoptosis in MCF-7 cells, as demonstrated by the detection of extracellular phosphatidylserine, which redistributes to the outer layer of the membrane during apoptosis. Early apoptotic cells demonstrated green fluorescence under microscopy. Necrotic cells were identified by their yellow-red intracellular staining appearance. DC induced apoptosis in a manner similar to that of 10 $\mu$M camptothecin (control compound). DC also decreased cell viability in MCF-7 cells in a dose-dependent manner ($IC_{50}$ of 13 $\mu$M) .

These biological activity data demonstrate the a specific licorice root extract, DC, has biological activity that is indicative of potential anti-tumorigenic effects in humans. Specifically, DC induces apoptosis and bcl-2 phosphorylation.

Thus, the present invention relates to compositions comprising a pure hydroxylated chalcone compound of *Glycyrrhiza glabra*. These compounds may be extracted and purified from *Glycyrrhiza glabra*. Alternatively, the hydroxylated chalcone compounds can be prepared synthetically using methods well known to those skilled in the art. Further, one of skill in-the art can now develop new compounds with similar structure and activity to the hydroxylated chalcone compounds of the present invention based on routine methods for testing of potential clinical compounds. Compositions of the present invention preferably further comprise an acceptable pharmaceutical vehicle for administration of the pure hydroxylated chalcone compound. Selection of acceptable pharmaceutical vehicles is performed routinely by those skill in the art and multiple formulation examples are provided in standard text references such as *Remington's Pharmaceutical Sciences*, Mack Publishing Co., Easton, Pa. 1985.

As demonstrated herein, compositions comprising a pure hydroxylated chalcone compound of *Glycyrrhiza glabra* induce bcl-2 phosphorylation in tissues and cells, in particular tumor cells or tissues, from animals, including humans. Compositions of the present invention are also useful in the induction of apoptosis in cells or tissues, in particular tumor cells or tissues, from animals, including humans. Thus, the compositions of the present invention are believed to be useful in methods for the prevention and treatment of cancer in animals, including humans. Accordingly, the present invention also relates to methods for prevention and treatment of cancer and tumor cell growth in animals, including humans, which comprises administering to the animal an effective amount of a composition containing a pure hydroxylated chalcone compound of *Glycyrrhiza glabra*. In the context of the present invention, by "effective amount" it is meant an amount of a pure hydroxylated chalcone compound of *Glycyrrhiza glabra* capable of producing a pharmacological response including, but limited to, induction of bcl-2 phosphorylation, induction of apoptosis, inhibition of tumorigenesis, or prevention or treatment of cancer. Effective amounts of the compounds to be administered can be determined routinely by those of skill in the art based upon pharmacological response data such as that provided herein. For example, doses to be administered are routinely determined by those skilled in the art based upon data from in vitro assays such as $IC_{50}$ determinations as provided in the instant application. Routes of administration, as well as dosing regimes, can also be determined routinely by one of skill in the art based upon prior experience with similar compounds, such as resveratrol.

The following non-limiting examples are presented to better illustrate the present invention.

EXAMPLES

Example 1

Extraction and Isolation of Licorice Root Compounds

Powdered roots of *Glycyrrhiza glabra* were extracted with methanol and concentrated under vacuum using rotary evaporation (Rotavapor R-110, Buchi, Switzerland). The remaining concentrate was then partitioned with acidified ethyl acetate (3% HCL). The dry ethyl acetate extract was then chromatographed on a reversed phase octadecyl-functionalized silica gel column such that bio-assay directed fractionation could be performed. Elution was done using a solvent mixture of water/methanol with an increasing concentration of methanol (90:10, 80:20, 70:30, 60:40, 50:50, 40:60, 30:70, 20:80, 10:90, 0:100; each 500 ml). Successive fractions were collected and tested for biological activity.

The most active fraction was re-chromatographed on a semi-preparative Zorbax Rx-C18 reversed phase HPLC column (9.4 mm×240 mm, 5 $\mu$m) purchased from Mac-Mod Analytical (Chadds Ford, Pa.). Compounds were eluted by a gradient solvent system (A: water and 0.05% formic acid; B: acetonitrile) . The elution program at 3 ml/min was as follows: 80% A to 40% B (0 to 45 minutes). The wavelength monitored was 254 nm. Successive fractions were collected and sent for additional biologic testing.

Fractions were screened for purity using a Discovery C18 reversed phase HPLC column (250 mm×4.6 mm; 5 $\mu$m) with a column guard purchased from Supelco (Bellefonte, Pa.).

The solvent program was a gradient system (A: water and 0.05% formic acid, B: 100% acetonitrile; 35 to 55 minutes). The elution program at 1 ml/minute was as follows: 100% A to 100% B (0 to 35 minutes); 100% B (35 to 55 minutes). The wavelengths monitored were 220 to 320 nm with a Varian 9065 diode array detector. Final separation of pure compounds was obtained using a semi-preparative HPLC on a Zorbax Rx-C18 reversed phase column (9.4 mm×240 mm, 5 μm) purchased from Mac-Mod Analytical. Compounds were eluted by a isocratic solvent system containing 82% water with 0.05% formic acid, 18% acetonitrile.

Example 2

Compound Identification

Both $^1$H and $^{13}$C NMR spectra were obtained on a VXR-200 instrument. Mass spectrometry was performed on a Micromass Platform II system equipped with a Digital DECPc XL560 computer for analysis of data. Mass spectra were obtained using atmospheric pressure chemical ionization (APCI) in the negative-ion mode. The ion source temperature was set at 150 C and the probe was set at 450 C. The sample cone voltage was 10 V and the corona discharge was 3.2 kV. HPLC analysis was performed on a Varian Vista 5500 liquid chromatograph pump coupled to a Varian 9065 Polychrom diode array detector. Semi-preparative fractionation of purified compounds was obtained on a Varian 9012 HPLC pump coupled to a Waters Lambda-Max Model 481 LC spectrophotometer. Octadecyl-functionalized silica gel (60A particle size) was used for column chromatography. The column packing was purchased from Aldrich Chemical Company (Milwaukee, Wis.). All solvents used for extraction and isolation were of HPLC grade.

Example 3

Bcl-2 Expression and Phosphorylation Assay

Analysis of bcl-2 protein expression was performed using a Western blot assay as previously described (Haldar, S. et al. 1996. *Cancer Res.* 56:1253; Haldar, S. et al. 1995. *Proc. Natl. Acad. Sci. USA* 92:4507–4511). Protein identification was made using a monoclonal bcl-2 primary antibody (DAKO Corporation) and secondary goat anti-mouse horseradish peroxidase conjugated antibody (Bio-Rad Laboratories, Richmond, CA). The phosphorylation of bcl-2 was determined by mobility shifts in the Western bolt as described by Haldar (Haldar, S. et al. 1996. *Cancer Res.* 56:1253; Haldar, S. et al. 1995. *Proc. Natl. Acad. Sci. USA* 92:4507–4511).

Example 4

Cell Cycle Analysis

Cells were treated for 24 hours, incubated with 10 μM BrdU for 45 minutes at 37° C. Cells were then washed with ice-cold PBS, resuspended in 200 μl PBS and fixed with cold 70% ethanol. The cells were resuspended, incubated for 30 minutes in 2 N HCl/0.5% Triton X-100 in PBS, and neutralized by rinsing once in 0.1 M sodium tetraborate (pH 8.5). Fluorescein isothiocyanate (FITC)-conjugated anti-BrdU antibody (Becton Dickinson) was added (10 μg/sample) in 50 μl of 0.5% Tween 20/1% BSA in PBS and incubated for 30 minutes. The cells were washed and resuspended in 1 ml of PBS containing 5 μg/ml propidium iodide. Fluorescence intensity was determined by quantitative flow cytometry and profiles were generated on a Becton Dickinson FACScan. A minimum of 10,000 cells were analyzed.

Example 5

Cell Viability and Apoptosis Assay

The Apoalert Annexin V-EGFP method (CLONTECH, Palo Alto, Calif.) was used to assess for apoptosis. Briefly, tumor cells were treated for 2 hours and cells were washed with fixing solution and stained with Annexin V-EGFP and propidium iodide for 15 minutes in the dark. Cells were viewed using a Nikin Eclipse TE-200 (Nikon Corporation, Tokyo, Japan) inverted fluorescent microscope. Photographs were captured using a SPOT digital camera (Diagnostic, Inc., Sterling Heights, Mich.) in combination with SPOT labeling with an APO-BRDU kit (Pharmingen, San Diego, Calif.). Cells (1×10$^6$ per dish) were treated for 12 hours, washed with PBS, and fixed in 1% paraformaldehyde in ice for 30 minutes. After fixation, cells were washed twice with PBS and fixed in 70% ethanol. The pellets were washed and resuspended in 50 μl of the DNA labeling solution containing Br-dUTP and TdT enzyme and incubated for 60 minutes at 37° C. After incubation, the pellets were washed, incubated with FITC labeled anti-BrdU antibody in the dark for 30 minutes at room temperature, and stained with propidium iodide and RNase. The stained cells were analyzed by flow cytometry after 30 minutes. Cell viability was assessed by the tetrazolium dye method as previously described (Scudiero, D.A. et al. 1988. *Cancer Res.* 48:4827–4833). Cells were plated in 96 well plates and incubated with various agents for 72 hours. Absorbance was measured at 570 nm using a Dyatech microplate reader.

Example 6

Microtubule Assay

Microtubule structure was assessed by indirect immunofluorescence as previously described (Zhang, C. C. et al. 1998. *Oncogene* 16:1617–1624). Cells were grown on coverslips and fixed in ice-cold methanol at −20° C. after drug treatment. The cells were then incubated with a 1:100 dilution of monoclonal anti-alpha-tubulin antibody (Clone DM 1A, mouse ascites fluid; Sigma) in 3% BSA in PBS for 30 minutes and washed in 3% BSA in PBS for 10 minutes. This was followed by incubation with FITC-goat anti-mouse IgG (1:50 dilution) as a secondary antibody for 30 minutes and washed in 3% BSA/PBS and visualized under a epifluorescent microscope (Zeiss AXIOSKOP) using a plan-NEOFLUAR 100 X oil immersion objective. The photographs were captured on a cooled CCD camera (DAGE-MTI) using Scion Image.

What is claimed is:

1. A method of inducing phosphorylation of bcl-2 in cells or tissues comprising contacting cells or tissues with a composition comprising 1-propanone-1-(2,4-dihydroxyphenyl)-3-hydroxy-3-(4'-hydroxyphenyl).

2. A method of inducing apoptosis in cells or tissues comprising contacting cells or tissues with the composition of claim 1.

3. A method of inhibiting growth of tumor cells comprising contacting tumor cells with a composition comprising 1-propanone-1-(2,4-dihydroxyphenyl)-3-hydroxy-3-(4'-hydroxyphenyl).

4. A method of preventing or treating cancer or tumor cell growth in an animal comprising administering to the animal a composition comprising 1-propanone-1-(2,4-dihydroxyphenyl)-3-hydroxy-3-(4'-hydroxyphenyl).

* * * * *